(12) United States Patent
Saudan et al.

(10) Patent No.: US 7,989,665 B2
(45) Date of Patent: Aug. 2, 2011

(54) HYDROGENATION OF ESTERS WITH RU/TETRADENTATE LIGANDS COMPLEXES

(75) Inventors: Lionel Saudan, Geneva (CH); Philippe Dupau, Bellegarde/Valserine (FR); Jean-Jacques Riedhauser, Dardagny (CH); Patrick Wyss, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/854,906

(22) Filed: Sep. 13, 2007

(65) Prior Publication Data
US 2008/0071098 A1  Mar. 20, 2008

Related U.S. Application Data

(63) Continuation of application No. PCT/IB2006/051028, filed on Apr. 4, 2006.

(30) Foreign Application Priority Data

Apr. 5, 2005 (WO) ................ PCT/IB2005/000938

(51) Int. Cl.
C07F 9/28 (2006.01)
C07C 29/17 (2006.01)
C07C 43/13 (2006.01)
C07D 307/00 (2006.01)
C07D 309/04 (2006.01)

(52) U.S. Cl. .......... 568/592; 568/599; 568/840; 556/21; 564/15; 549/423

(58) Field of Classification Search ................ 568/814, 568/885
See application file for complete search history.

(56) References Cited

U.S. PATENT DOCUMENTS

| 2004/0015017 A1 | 1/2004 | Rautenstrauch et al. ..... 564/490 |
| 2004/0063966 A1 | 4/2004 | Rautenstrauch et al. ..... 548/400 |

FOREIGN PATENT DOCUMENTS

| GB | 2 031 883 A | 4/1980 |
| WO | WO 02/22526 A2 | 3/2002 |
| WO | WO 02/40155 A1 | 5/2002 |

OTHER PUBLICATIONS

J-X Gao et al., XP-001038642,"New Chiral Catalysts for Reduction of Ketones", Chirality, vol. 12, pp. 383-388 (2000).
International Search Report and Written Opinion of the International Searching Authority dated Aug. 9, 2006 from application No. PCT/IB2006/051027.

*Primary Examiner* — Sikarl Witherspoon
(74) *Attorney, Agent, or Firm* — Winston & Strawn LLP

(57) ABSTRACT

The present invention relates to the field of catalytic hydrogenation and, more particularly, to the use of Ru complexes with tetradentate ligands having at least one amino or imino coordinating group and at least one phosphino coordinating group in hydrogenation processes for the reduction of esters or lactones into the corresponding alcohol or diol respectively.

14 Claims, No Drawings

HYDROGENATION OF ESTERS WITH RU/TETRADENTATE LIGANDS COMPLEXES

CROSS-REFERENCE TO RELATED APPLICATION(S)

This application is a continuation of International application PCT/IB2006/051028 filed on Apr. 4, 2006, the entire content of which is expressly incorporated herein by reference thereto.

TECHNICAL FIELD

The present invention relates to the field of catalytic hydrogenation and, more particularly, to the use of Ru complexes with tetradentate ligands, in hydrogenation processes for the reduction of esters or lactones into the corresponding alcohol or diol respectively.

BACKGROUND

Reduction of an ester functional group to the corresponding alcohol is one of the fundamental reactions in organic chemistry, and is used in a large number of chemical processes. In general, two main types of processes are known to achieve such a transformation. Such types of processes are the following:
a) hydride processes, in which a silyl or metal hydride salt, such as LiAlK, is used;
b) hydrogenation processes, in which molecular hydrogen is used.

From a practical point of view, hydrogenation processes are more attractive as they can be run using small amounts of catalyst (typically 10 to 1000 ppm relative to the substrate) and in the presence of small quantities or even in the absence of solvent. Furthermore, hydrogenation processes do not require the use of highly reactive and expensive hydrides, and do not produce important amounts of aqueous waste.

One of the mandatory and characterizing elements of hydrogenation processes is the catalyst or the catalytic system which is used to activate the molecular hydrogen in view of the reduction. The development of useful catalysts or catalytic systems for the hydrogenation of an ester functional group represents still an important need in chemistry.

Amongst the few catalysts or catalytic systems known to perform such reductions one may cite the ruthenium/phosphine complexes, obtained by the reaction of ruthenium oxide or carboxylate precursor with a mono-, di- or tri-phosphine ligand (an example of which is described by Elsevier et al. in Chem. Commun., 1998, 1367). In this type of complex the ruthenium metal is coordinated only by "acac" ligands and phosphine atoms, limiting thus the diversity of the ligand structure and coordination sphere around the metal center. As a consequence of such little diversity the tuning of the activity and of the performance of the hydrogenation process is not easy. Furthermore, the experimental conditions require very high pressures (at least 70-130 bars) and temperatures (120-180° C.).

Therefore, there is a need for hydrogenation processes using alternative catalysts or pre-catalysts, preferably having a greater diversity in the ligand structures and coordination spheres around the metal center and allowing the use of softer experimental conditions.

SUMMARY OF THE INVENTION

The present invention now relates about a hydrogenation process for the reduction of esters, or the like, into alcohols in the presence of a base and at least one complex in the form of a ruthenium complex of a tetradentate ligand wherein the coordinating groups consist of two amino or imino group and two phosphino group. The invention relates also about new ligands and complexes useful for carrying the invention process.

DETAILED DESCRIPTION OF THE PREFERRED EMBODIMENTS

In order to overcome the problems aforementioned, the present invention relates to processes for the reduction by hydrogenation, using molecular $H_2$, of a $C_3$-$C_{70}$ substrate containing one or two esters, or lactones, functional groups into the corresponding alcohol, or diol, characterized in that the process is carried out in the presence of a base and at least one catalyst or pre-catalyst in the form of a ruthenium complexes of a tetradentate ligand wherein the coordinating groups consist of at least one amino or imino group and at least one phosphino group.

According to a particular embodiment of the invention, the substrate can be a compound of formula (I)

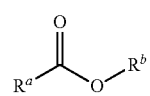

wherein $R^a$ and $R^b$ represent, simultaneously or independently, a linear, branched or cyclic $C_1$-$C_{30}$ aromatic, alkyl or alkenyl group, optionally substituted; or
$R^a$ and $R^b$ are bonded together and form a $C_4$-$C_{20}$ saturated or unsaturated group, optionally substituted.

The corresponding alcohols (i.e. (II-a) and (II-b)), or the corresponding diol (II'), of the substrate (I), are of formula

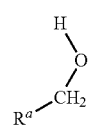

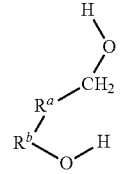

wherein $R^a$ and $R^b$ are defined as in formula (I).

A compound of formula (II) (i.e. II-a or II-b) will be obtained in the case where $R^a$ and $R^b$ are not bonded together, while a compound of formula (II') will be obtained in the case where $R^a$ and $R^b$ are bonded together.

It is understood that by "a linear, branched or cyclic . . . aromatic, alkyl, or alkenyl group" it is meant that the $R^a$ or $R^b$ can be in the form of, e.g., a linear alkyl group or can also be in the form of a mixture of the type of groups, e.g. a specific $R^a$ may comprises a linear alkyl, a branched alkenyl, a (poly)

cyclic alkyl and an aryl moiety, unless a specific limitation to only one type is mentioned. Similarly, in all the below embodiments of the invention when a group is mentioned as being in the form of more than one type of topology (e.g. linear, cyclic or branched) and/or unsaturation (e.g. alkyl, aromatic or alkenyle) it is meant also a group which may comprise moieties having any one of the topologies or unsaturations, as above explained.

A particular embodiment of the invention's process is shown in Scheme 1:

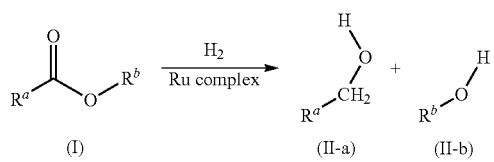

According to a further embodiment of the invention, the substrate is an ester, or lactone, that will provide an alcohol, or a diol, that is useful in the pharmaceutical, agrochemical or perfumery industry as final product or as an intermediate. Particularly preferred substrate is an ester, or lactone, that will provide an alcohol, or diol, which is useful in the perfumery industry as final product or as an intermediate.

According to another embodiment of the invention, the substrate is a $C_5$-$C_{30}$ compound of formula (I), and in particular one may cite those wherein $R^a$ and $R^b$ represent simultaneously or independently a linear, branched or cyclic $C_1$-$C_{30}$ aromatic or alkyl group optionally substituted, or a cyclic $C_5$-$C_{30}$ alkenyl group optionally substituted; or R and $R^b$ are bonded together and form a $C_4$-$C_{20}$ saturated or unsaturated linear, branched, mono-, di- or tri-cyclic group, optionally substituted.

According to a further embodiment of the invention the substrate is a $C_5$-$C_{20}$ compound of formula (I), wherein $R^a$ and $R^b$ represent simultaneously or independently a linear, branched or cyclic $C_5$-$C_{18}$ aromatic or alkyl group, optionally substituted, or a cyclic $C_5$-$C_{18}$ alkenyl group, optionally substituted; or $R^a$ and $R^b$ are bonded together and form a $C_4$-$C_{20}$ saturated or unsaturated linear, branched, mono-, di- or tri-cyclic group, optionally substituted.

Furthermore, according to a yet further embodiment, when $R^a$ and/or $R^b$ represent an alkenyl group then the carbon-carbon double bond is not terminal and is not conjugated.

Possible substituents of $R^a$ and $R^b$ are one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group, preferably a $C_1$ to $C_4$ linear or branched alkyl or alkenyl group. As other possible substituents one may also cite a group $COOR^c$, which can also be reduced to the corresponding alcohol during the invention's process, according to the molar amount of $H_2$ used, as well known by a person skilled in the art.

Non-limiting examples of substrates are alkyl cinnamates, sorbates or salycilates, alkyl esters of natural (fatty or not) acids, Sclareolide, spirolactones, allylic ester, di alkyl diesters, (un)substituted benzoic esters, and β-γ unsaturated esters. In particular, the substrate can be selected from the group consisting of sclareolide, $C_9$-$C_{15}$ spirolactones and $C_1$-$C_4$ alkyl esters of 4-methyl-6-(2,6,6-trimethyl-1-cyclohexen-1-yl)-3-hexenoic acid. One can also cite the di alkyl esters of 1,4-dicarboxylate-cyclohexane, the di $C_{1-5}$ alkyl esters of the $C_{2\text{-}10}$ alkanediyl-dicarboxylates, $C_{1\text{-}5}$ alkyl cyclopropanecarboxylates, mono-, di- or tri-methoxybenzoic esters.

The process of the invention is characterized by the use, as catalyst or pre-catalyst (hereinafter referred to as complexes unless specified otherwise), of a ruthenium complex as described above. The complex can be in the form of an ionic or neutral species.

According to an embodiment of the invention, the ruthenium complex can be of the general formula

wherein L4 represents a tetradentate ligand wherein the coordinating groups consist of at least one amino or imino group and at least one phosphino group; and each Y represents, simultaneously or independently, CO, a hydrogen or halogen atom, a hydroxyl group, or a $C_1$-$C_6$ alkoxy or carboxylic radical, or also a $BH_4$ or $AlH_4$ group;

X represents a $C_3$-$C_{30}$ mono-phosphine or a solvent;

Z represents a non-coordinated anion; and n is 0, 1 or 2.

In particular L4 is a tetradentate ligand, such as a $C_8$-$C_{45}$ compound, wherein the coordinating groups consist of two amino or imino group and two phosphino group, and in particular the amino groups are a primary (i.e. $NH_2$) or a secondary (i.e. NH) amino groups.

In a particular embodiment of the invention, in formula (1) or (2), each Y represents, simultaneously or independently, a hydrogen or chlorine atom, a hydroxy radical, a $C_1$ to $C_6$ alkoxy radical, such as a methoxy, ethoxy or isopropoxy radical, or a $C_1$ to $C_6$ acyloxy radical such as a $CH_3COO$ or $CH_3CH_2COO$ radical. More preferably, each Y represents, simultaneously or independently, a hydrogen or chlorine atom, a methoxy, ethoxy or isopropoxy radical, or a $CH_3COO$ or $CH_3CH_2COO$ radical.

In a particular embodiment of the invention, in formula (2), X represents a mono-phosphine of formula $PR^d_3$, wherein $R^d$ is a $C_1$-$C_{12}$ group, such as linear, branched or cyclic alkyl, alkoxy or aryloxy group optionally substituted, substituted or unsubstituted phenyl, diphenyl or naphthyl or di-naphthyl group. More particularly $R^d$ may represent a substituted or unsubstituted phenyl, diphenyl or naphthyl or di-naphthyl group. Possible substituents are those cited below for L4.

X may also be a solvent, the term "solvent" has to be understood according to the 10 usual meaning in the art and includes compounds used as diluent in the preparation of the complex or during the invention's process, non limiting examples are dimethylsulfoxide, acetonitrile, dimethylformamide, an alcohol (e.g. an $C_1$-$C_4$ alcohol), or also THF, acetone, pyridine or a $C_3$-$C_8$ ester or the substrate of the invention's process.

In a particular embodiment of the invention, in formula (2), Z represents a halogen 15 atom, a hydroxyl group, or a $C_1$-$C_6$ alkoxy, phenoxy or carboxylic radical.

The complex of formula (1) represents, in general for practical reasons, a preferred embodiment of the invention.

According to a particular embodiment of the invention, L4 can be a compound of formula

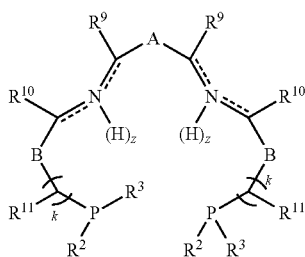

(3)

wherein the dotted lines indicate a single or double bond, z is 1 if the nitrogen atom belongs to an amino group (the dotted lines are single bonds) or is 0 if the nitrogen atom belongs to an imino group (one dotted line is a double bond);

$R^2$ and $R^3$, when taken separately, represent, simultaneously or independently, a linear, branched or cyclic $C_1$ to $C_8$ alkyl or alkenyl group optionally substituted, a $C_6$ to $C_{10}$ aromatic group optionally substituted, or an $OR^{2'}$ or $NR^{2'}R^{3'}$ group, $R^{2'}$ and $R^{3'}$ being a $C_1$ to $C_8$ alkyl or alkenyl group; or the groups $R^2$ and $R^3$ bonded to the same P atom, when taken together, form a saturated or unsaturated ring optionally substituted, having 4 to 10 atoms and including the phosphorus atom to which the $R^2$ and $R^3$ groups are bonded;

A represents a $-(CR^9{}_2)_k-$ group or a diphenyl, dinaphthyl, $C_5$-$C_{12}$ metallocediyl, phenylene ($-C_6H_4-$) or naphthylene ($-C_{10}H_6-$) group optionally substituted;

B represents a diphenyl, dinaphthyl, $C_5$-$C_{12}$ metallocediyl, phenylene or naphthylene group optionally substituted or a group of formula

(i)

$R^9$, $R^{10}$ and $R^{11}$, taken separately, represent, simultaneously or independently, a hydrogen atom, a $C_1$-$C_{10}$ linear, branched or cyclic alkyl or alkenyl group optionally substituted or a $C_6$ to $C_{10}$ aromatic group optionally substituted; two adjacent or geminal $R^9$, taken together, may form a $C_{5\text{-}10}$ ring including the carbon atom to which the $R^9$ groups are bonded; a $R^{10}$ group and a $R^9$ group, in α-position to the same N atom, can be bonded together to form a $C_4$-$C_6$ saturated or unsaturated ring; two adjacent $R^{11}$ groups can be bonded together to form a $C_5$ to $C_{10}$ aromatic ring optionally substituted or a $C_5$-$C_{12}$ metallocenediyl group optionally substituted and including the carbon atom to which the $R^{11}$ or $R^9$ groups are bonded; and k are, simultaneously or independently, equal to 0 or 1.

It is understood that, in any of the present embodiments, the metallocenediyl, such as for example a ferrocenediyl, can be in the form of a metallocene-1,1'-diyl or of a metallocene-1,2-diyl.

Similarly when A and/or B are diphenyl or dinaphthyl groups they are preferably in their 1,1' form, and when the A and/or B are phenylene or naphthylene group they are in a ortho or meta form or for the naphthylene also as naphthalene-1,8-diyl derivative.

According to a particular embodiment of the invention, 1,4 can be a compound of formula (4-A) or (4-B):

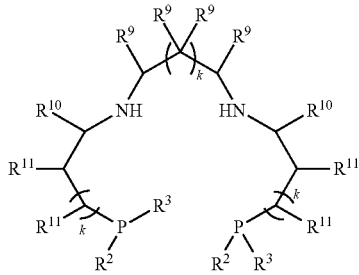

(4-A)

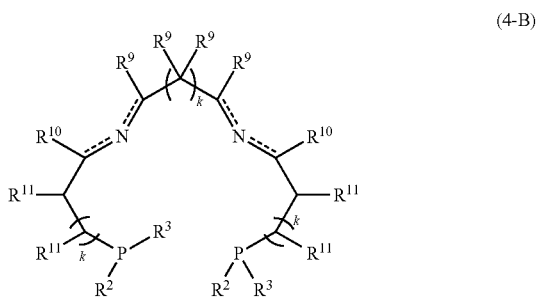

(4-B)

wherein the dotted lines indicate a single or double bond;

$R^2$ and $R^3$, when taken separately, represent, simultaneously or independently, a linear, branched or cyclic $C_1$ to $C_8$ alkyl or alkenyl group optionally substituted, a $C_6$ to $C_{10}$ aromatic group optionally substituted, or an $OR^{2'}$ or $NR^{2'}R^{3'}$ group, $R^{2'}$ and $R^{3'}$ being a $C_1$ to $C_8$ alkyl or alkenyl group; or the groups $R^2$ and $R^3$, when taken together, form a saturated or unsaturated ring optionally substituted, having 4 or 5 to 10 atoms and including the phosphorus atom to which the $R^2$ and $R^3$ groups are bonded;

$R^9$, $R^{10}$ and $R^{11}$, taken separately, represent, simultaneously or independently, a hydrogen atom, a $C_1$-$C_8$ linear, branched or cyclic alkyl or alkenyl group optionally substituted or a $C_6$ to $C_{10}$ aromatic group optionally substituted; two adjacent or geminal $R^9$, taken together, may form a, preferably $C_5$ to $C_8$, ring including the carbon atom to which the $R^9$ groups are bonded; a $R^{10}$ group and a $R^9$ group, in α-position to the same N atom, can be bonded together to form a $C_4$-$C_6$ ring; two adjacent $R^{11}$ groups can be bonded together to form a $C_6$ to $C_{10}$ aromatic ring optionally substituted or a $C_5$-$C_{12}$ metallocenediyl group optionally substituted and including the carbon atom to which the $R^{11}$ groups are bonded; and k are, simultaneously or independently, equal to 0 or 1.

According to an embodiment of the invention, $R^2$ and $R^3$ may represent, simultaneously or independently, a linear, branched or cyclic $C_1$ to $C_6$ alkyl group optionally substituted, a phenyl group optionally substituted; the groups $R^2$ and $R^3$, taken together, may form a saturated or unsaturated ring optionally substituted, having 4, 5, 6 or 7 atoms and including the phosphorus atom to which the $R^2$ and $R^3$ groups are bonded. Alternatively, $R^2$ and $R^3$ may represents a linear, branched or cyclic $C_1$ to $C_6$ alkyl group optionally substituted or an phenyl group optionally substituted.

Preferably, ligand L4 is a compound of formula

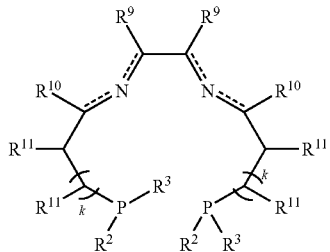
(4-C)

wherein the dotted lines indicate a single or double bond;

$R^2$ and $R^3$, taken separately, represent simultaneously or independently a linear, branched or cyclic alkyl group containing 1 to 6 carbon atoms or a phenyl group optionally substituted; or the two $R^2$ and $R^3$ bonded to the same P atom, taken together, form a ring having 5 to 7 atoms and including the phosphorus atom to which they are bonded;

$R^9$, $R^{10}$ and $R^{11}$, taken separately, represent, simultaneously or independently, a hydrogen atom, a $C_1$-$C_4$ linear or branched alkyl group optionally substituted or a phenyl group optionally substituted; the two $R^9$, taken together, may form a $C_4$-$C_8$, or preferably a $C_5$-$C_7$, ring including the carbon atom to which the $R^9$ groups are bonded; two adjacent $R^{11}$, taken together, may form a phenyl group optionally substituted and including the carbon atom to which the $R^{11}$ groups are bonded; and k are, simultaneously or independently, equal to 0 or 1.

Possible substituents of the various groups A, B, $R^2$, $R^3$, $R^9$, $R^{10}$ and $R^{11}$ are one or two halogen, $C_1$ to $C_{10}$ alkoxy, polyalkyleneglycols, halo- or perhalo-hydrocarbon, COOR, $NR_2$, quaternary amine or R groups, wherein R is a $C_1$ to $C_6$ alkyl, or a $C_5$ to $C_{12}$ cycloalkyl, aralkyl (such as benzyl, phenethyl etc.) or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups. By "halo- or perhalo-hydrocarbon" it is meant groups such as $CF_3$ or $CClH_2$ for instance.

Alternatively the substituents can be, and in particular when the groups are or contain phenyl groups or moieties, one or two halogen, $C_1$ to $C_5$ alkoxy or polyalkyleneglycols groups, COOR, $NR_2$ or R groups wherein R is a $C_1$ to $C_4$ alkyl, or a $C_{5-6}$ cycloalkyl, aralkyl or aromatic group, the latter being also optionally substituted as above defined.

Alternatively, possible substituents of $R^9$, $R^{10}$ and $R^{11}$ are one or two halogen atoms or $R^8$, $OR^8$ or $NR^8{}_2$, $R^8$ being a $C_1$ to $C_6$ alkyl groups or a $C_1$ to $C_4$ alkyl groups.

According to a specific embodiment of the invention the complexes of the formula (1) or (2) wherein Y is defined as above, and in particular represents H or Cl, and L4 represent a ligand of the formulae (4-D), (4-E), (4-F) or (4-G):

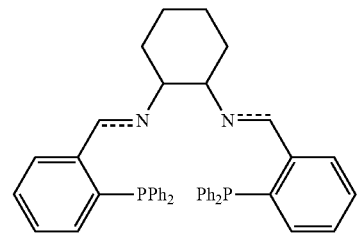
(4-D)

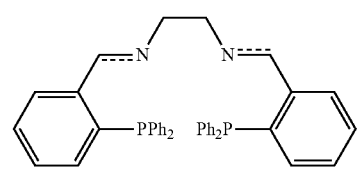
(4-E)

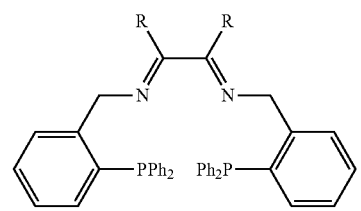
(4-F)

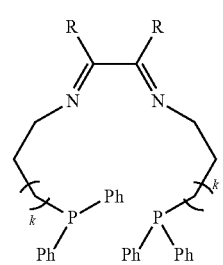
(4-G)

wherein the dotted lines represent a single or double bond and Ph is a phenyl radical, R, taken separately, is $C_1$-$C_5$ alkyl or, taken together, are a $C_3$-$C_6$ group, and k is 1 or 0.

The ligands of one of the formulae

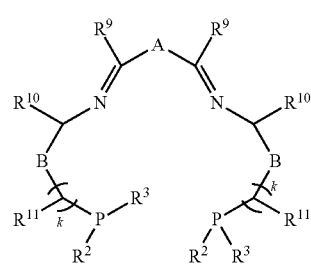
(2')

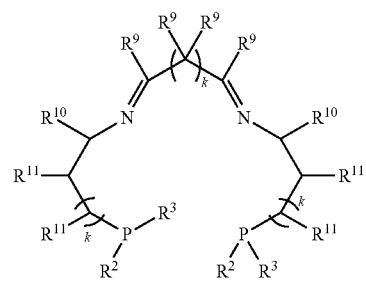
(4-B')

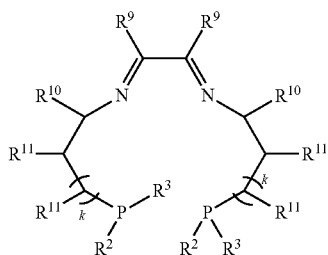

(4-C')

wherein A, B, $R^2$, $R^3$, $R^9$, $R^{10}$, $RK^{11}$ and k have the same meaning as above, as well as those of formula (4-F) or (4-G) are new, with the exception of N,N'-1,2-ethanediylidenebis[2-(diphenylphosphino-) benzenemethanamine and of N,N'-2,3-butanediylidenebis[2-(diphenylphosphino-) benzenemethanamine, and are therefore also an object of the present invention.

Similarly the invention complexes where the tetradentate ligand is a compound of formula (2'), (4-B'), (4-C'), (4-F) or (4-G) are also new, with the exception of dichloro[N,N'-1,2-ethanediylidenebis[2-(diphenylphosphino-κP)benzenemethanamine-κN]]-Ruthenium, and are also an object of the present invention.

The ligands described above can be obtained by applying standard methods which are well known in the state of the art and by the person skilled in the art. Therefore, their preparation does not require a specific description. For example one may revert to WO 02/40155.

In general, the complexes of formula (1) can be prepared and isolated prior to their use in the process according to the general methods described in the literature. A method is described in the Example.

Moreover, the complexes can be prepared in situ, by several methods, in the hydrogenation medium, without isolation or purification, just before their use.

One of the possible procedures to advantageously prepare in situ a complex of formula (1) consists in reacting an appropriate Ru complex of formula [Ru("diene")("allyl")$_2$], wherein "diene" represents a cyclic or linear hydrocarbon containing two carbon-carbon double bonds, conjugated or not, such as for example 1,5-cyclooctadiene (COD) or norbornadiene, and "allyl" represents a linear or branched $C_3$ to $C_8$ hydrocarbon radical containing one carbon-carbon double bond such as methylallyl or allyl, with a non coordinating acid such as $HBF_4$-$Et_2O$, and then treating the resulting solution with the required amount of a ligands L4, such as defined previously, to give a solution of a catalyst according to formula (1). Furthermore, the mixture thus obtained can also be treated with a base in the presence of a primary or secondary alcohol. Furthermore, the complexes of formula (1) can be prepared by reacting an appropriate Ru complex such as, [RuCl$_2$(PPh$_3$)$_3$], [RuCl$_2$(cod)] or [RuCl$_2$(arene)]$_2$ with the required amount of a ligands L4, such as defined previously (cod representing a cyclooctadiene and arene being e.g. a benzene or naphthalene).

It is also understood that the complex of formula (I) can also be obtained in situ from complexes which have a similar formula and which in presence of, for example an alcohol and a base, are converted into a compound of formula (I). For example, from a complex wherein X, Y, and Z have other meaning.

To carry out the processes of the invention it is required also to use a base. The base can be the substrate itself, if the latter is basic, a corresponding alcoholate or any base having preferentially a $pK_a$ above 11. According to a particular embodiment of the invention the base may have a $pK_a$ above 14. It is also understood that preferably the base does not reduce itself a substrate of formula (I). As non-limiting examples one may cite the following type of base: alcoholate, hydroxides, alkaline or alkaline-earth carbonates, phosphazenes, amides, basic alox, siliconates (i.e. silicium derivatives having SiO— or SiRO— groups), hydrides such as $NaBH_4$, NaH or KH.

One can cite, as non-limiting examples, alkaline or alkaline-earth metal carbonates, such as cesium carbonate, an alkaline or alkaline-earth metal hydroxides, $C_{1-10}$ amidures, $C_{10-26}$ phosphazene or an alcoholate of formula $(R^{13}O)_2M$ or $R^{13}OM'$, wherein M is an alkaline-earth metal, M' is an alkaline metal or an ammonium $NR^{14}{}_4^+$, $R^{13}$ stands for hydrogen or a $C_1$ to $C_6$ linear or branched alkyl radical and $R^{14}$ stands for a $C_1$ to $C_{10}$ linear or branched alkyl radical, such as sodium or potassium alcoholates. Of course, other suitable bases can be used.

According to an embodiment of the invention, the base is an alkaline alcoholate of formula $R^{13}OM'$.

As previously mentioned the processes of the invention consist in the hydrogenation of a substrate using a ruthenium complex and a base. A typical process implies the mixture of the substrate with the ruthenium complex, a base and optionally a solvent, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 50 ppm to 50000 ppm, relative to the amount of substrate. Preferably, the complex concentration will be comprised between 100 and 20000 ppm. It goes without saying that the optimum concentration of complex will depend, as the person skilled in the art knows, on the nature of the latter, on the nature of the substrate and on the pressure of $H_2$ used during the process, as well as the desired time of reaction.

Useful quantities of base, added to the reaction mixture, may be comprised in a relatively large range. One can cite, as non-limiting examples, ranges between 5 to 50000 molar equivalents, relative to the complex (e.g. base/com=5 to 50000), preferably 20 to 2000, and even more preferably between 50 and 1000 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as toluene or xylene, hydrocarbon solvents such as hexane or cyclohexane, ethers such as tetrahydrofuran or MTBE, polar solvents such as primary or secondary alcohols such as isopropanol or ethanol, or mixtures thereof. The choice of the solvent is a function of the nature of the complex and the person skilled in the art is well able to select the solvent most convenient in each case to optimize the hydrogenation reaction.

In the hydrogenation process of the invention, the reaction can be carried out at a $H_2$ pressure comprised between $10^5$ Pa and $80 \times 10^5$ Pa (1 to 80 bars) or even more if desired. Again, a person skilled in the art is well able to adjust the pressure as a function of the catalyst load and of the dilution of the substrate in the solvent. As examples, one can cite typical pressures of 1 to $50 \times 10^5$ Pa (1 to 50 bar).

The temperature at which the hydrogenation can be carried out is comprised between 0° C. and 120° C., more preferably in the range of between 50° C. and 100° C. Of course, a person skilled in the art is also able to select the preferred temperature as a function of the melting and boiling point of the starting and final products as well as the desired time of reaction or conversion.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in open glass tubes placed inside a stainless steel autoclave. $H_2$ gas (99.99990%) was used as received. All substrates and solvents were distilled from appropriate drying agents under Ar. NMR spectra were recorded on a Bruker AM-400 ($^1$H at 400.1 MHz, $^{13}$C at 100.6 MHz, and $^{31}$P at 161.9 MHz) spectrometer and normally measured at 300 K, in $CDCl_3$ unless indicated otherwise. Chemical shifts are listed in ppm.

Example 1

Preparation of N,N'-bis{[2-(diphenylphosphino)phenyl]methylene}-2,2-dimethyl-1,3-propanediamine (L-5)

Under argon, a solution of 2-(diphenylphosphino)benzaldehyde (522.7 mg, 1.8 mmol) and 2,2-dimethyl-1,3-propanediamine (93.3 mg, 0.9 mmol) in toluene (15 mL) was stirred at room temperature for 15 h. Then the reaction mixture was heated at 80° C. (oil bath) for 2 h 30 min. Next, the solvent was removed in vacuo, and an orange solid was recovered (476.8 mg, 0.74 mmol, 82%).

$^1$H NMR ($CD_2Cl_2$, 400 MHz): δ 8.78 (d, J=4.6 Hz, 2H), 7.96 (dd, J=7.7, 4.1 Hz, 2H), 7.3-7.2 (m, 24H), 6.87 (dd, J=7.7, 4.1Hz, 2H), 3.19 (s, 4H), 0.69 (s, 6H).

$^{13}$C NMR ($CD_2CL_2$, 100 MHz): δ 160 (d, J=20.2 Hz, CH=N), 140.3 (d, J=17.8 Hz, Carom), 137.7 (d, J=20.2 Hz, Carom), 137.4 (d, J=10.5 Hz, Carom), 134.4 (d, J=20.2 Hz, CHarom), 134.1 (d, J=20.2 Hz, CHarom), 133.7 (CHarom), 130.2 (CHarom), 129.1 (CHarom), 128.9 (d, J=7.3 Hz, CHarom), 128.4 (d, J=4.8 Hz, CHarom), 70.7 (CH2), 36.9 (C), 24.4 (CH3).

$^{31}$P{$^1$H} NMR ($CD_2CL_2$, 100 MHz): δ –12.8.

This ligand is a novel one, as well as the ruthenium complex comprising it.

Example 2

Catalytic Hydrogenation of Various Esters Using Complexes of Formula (1)

a) Using Pre-Formed Complex

A typical catalytic hydrogenation using preformed $RuCl_2$(L-1) as pre-catalyst is described below with methyl benzoate as substrate:

Under argon, a solution of methyl benzoate (2.721 g, 20 mmol) in THF (2 mL) was added with a syringe, followed by more THF (2×1 mL), to a Keim autoclave equipped with a glass liner containing $RuCl_2$(L-1) (7.9 mg, 0.01 mmol, 0.05 mol %), solid NaOMe (107.9 mg, 2.0 mmol, 10 mol %) and THF (10 mL). The autoclave was pressurised with hydrogen gas at 50 bars and placed in a thermosttated oil bath set at 100° C. After 2 h 30 min, the autoclave was removed from the oil bath, and cooled in a cold-water bath. Then, the reaction mixture was diluted with aq. 1N HCl (50 mL) and extracted with MTBE (100 mL). Gas chromatography after silylation of an aliquot showed the following products: methyl benzoate (1.7%), benzyl alcohol (94.6%), benzoic acid (3.7%). Then, the organic phase was washed successively with aq. 1N KOH (50 mL) and aq. sat. NaCl (3×50 mL), and dried over $MgSO_4$ anh. Filtration and removal of the solvent in vacuo gave a yellow liquid (2.085 g). Purification by flash chromatography on silica gel with pentane/$Et_2O$ (2/1) as elution mixture gave pure benzyl alcohol (1.742 g, 16.1 mmol, 80%) as a colourless liquid.

$^1$H NMR ($CDCl_3$, 400 MHz): δ 7.38-7.25 (m, 5H), 4.65 (s, 2H), 2.02 (s, 1H).

$^{13}$C NMR ($CDCL_3$, 100 MHz): δ 140.9 (s), 128.6 (d), 127.6 (d), 126.9 (d), 62.3 (t).

b) Using in-situ Formed Complex

A typical catalytic hydrogenation using in-situ formed $RuCl_2$(L-4) as pre-catalyst is described below with methyl benzoate as substrate:

Under argon, a solution of methyl benzoate (2.723 g, 20 mmol) in THF (2 mL) was added with a syringe, followed by more THF (2×1 mL), to a Keim autoclave equipped with a glass liner containing [$RuCl_2$(para-cymene)]$_2$ (6.5 mg, 0.01 mmol, 0.05 mol %), ligand L-4 (12.2 mg, 0.02 mmol, 0.1 mol %), solid NaOMe (108.1 mg, 2.0 mmol, 10 mol %) and THF (10 mL). Then a solution of tridecane (368.8 mg, 0.02 mmol), as internal standard, is added in THF (2 mL), followed by more THF (2×1 mL). The autoclave was then pressurised with hydrogen gas at 50 bars and placed in a thermostatted oil bath set at 100° C. After 2 h 30 min, the autoclave was removed from the oil bath, and cooled in a cold-water bath. Then, the reaction mixture was diluted with MTBE (100 mL) and washed successively with aq. 1N HCl (50 mL) and aq. sat. NaCl (3×50 mL). Gas chromatography after silylation of an aliquot showed the following products: benzyl alcohol (97.4%), benzoic acid (2.6%). GC yield based on the internal standard gave a yield of 90% of benzyl alcohol.

Using methyl benzoate as a test substrate several complexes (Table 1), bases and solvent, as reported in Table 2, were tested under these conditions.

TABLE 1

Structure of ligands

| Structure | Name |
| --- | --- |
| 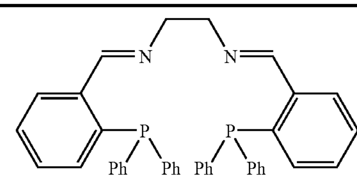 | L-1 |
| 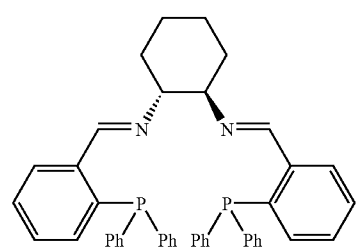 | L-2 |

TABLE 1-continued

Structure of ligands

| Structure | Name |
|---|---|
| (diagram: ethylenediamine-based ligand with two -NH-CH2-C6H4-PPh2 arms) | L-4 |
| (diagram: neopentyl-based diimine ligand with two =N-CH=C6H4-PPh2 arms) | L-5 |
| (diagram: diketimine ligand with two -CH2CH2-PPh2 arms) | L-6 |

Ligands L-1 to L-4 were prepared according to Rautenstrauch, V. et al in WO 02/40155. Ligand L-6 was prepared according to DuBois, T. D. *Inorganic Chem.* 1972, 11(4), 718-722.

TABLE 2

Hydrogenation of methyl benzoate using complexes of formula (1)

| Test | Complex | Com/Base[1] | Base | Solvent | GC yield (%)[2] |
|---|---|---|---|---|---|
| 1 | RuCl$_2$(L-1) | 1000/1000000 | NaOMe | THF | 86[3] |
| 2 | RuCl$_2$(L-1) | 1000/100000 | NaOMe | THF | 95[3] |
| 3 | RuCl$_2$(L-1) | 500/100000 | NaOMe | THF | 95 (81) |
| 4 | RuCl$_2$(L-1) | 500/100000 | NaOMe | THF[4] | 77 |
| 5 | RuCl$_2$(L-1) | 500/100000 | NaOMe | THF[5] | 34 |
| 6 | RuCl$_2$(L-1) | 500/100000 | NaOMe | Toluene | 92 |
| 7 | RuCl$_2$(L-1) | 500/100000 | NaOMe | iPrOH | 73 |
| 8 | RuCl$_2$(L-1) | 500/100000 | NaO$^i$Pr | THF | 93 |
| 9 | RuCl$_2$(L-2) | 500/100000 | NaOMe | THF | 99 |
| 10 | RuCl$_2$(L-4) | 1000/100000 | NaOMe | THF[6] | 97 |
| 11 | RuCl$_2$(L-5) | 1000/100000 | NaOMe | THF[7] | 96 |
| 12 | RuCl$_2$(L-6) | 1000/100000 | NaOMe | THF[8] | 99 |

Reaction conditions: Substrate (20 mmol), H$_2$ gas (50 bars), THF (14 mL) at 100° C. during 2 h 30 min.
[1] Com/Base: complex/base molar ratio in ppm relative to the substrate.
[2] Based on internal standard (analysed by GC) otherwise indicated. In brackets isolated yield after chromatography on silica gel.
[3] Conversion (in %, analysed by GC) of methyl benzoate into benzyl alcohol after 1 hour.
[4] Reaction run at 60° C. during 6 h.
[5] Reaction run with H$_2$ gas (10 bars) during 6 h.
[6] Complex generated in-situ with L-4 and [RuCl$_2$(para-cymene)]$_2$
[7] Complex generated in-situ with L-5 and [RuCl$_2$(para-cymene)]$_2$
[8] Complex generated in-situ with L-6 and [RuCl$_2$(para-cymene)]$_2$ and reaction run during 1 hour.

Several other esters, whose structure and names are described in Table 3, were hydrogenated under the conditions described above using preformed RuCl$_2$(L-1). Isolated yield are given in Table 4.

TABLE 3

Structure and names of substrates used

| Substrate | Structure | Name |
|---|---|---|
| 1 | (methyl benzoate structure) | Methyl benzoate |
| 2 | (iso-propyl benzoate structure) | iso-Propyl benzoate |
| 3 | (methyl 4-methoxybenzoate structure) | Methyl 4-(methoxy) benzoate |

TABLE 3-continued

Structure and names of substrates used

| Substrate | Structure | Name |
|---|---|---|
| 4 | 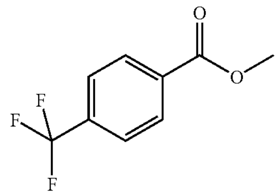 | methyl 4-(trifluoromethyl) benzoate |
| 5 | 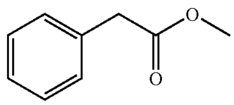 | Methyl phenylacetate |
| 6 | 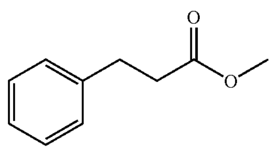 | Methyl 3-(phenyl) propanoate |
| 7 | 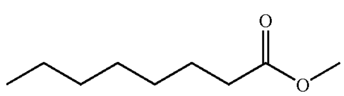 | Methyl octanoate |
| 8 | 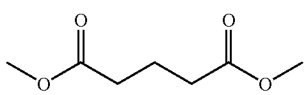 | Dimethyl glutarate |
| 9 | 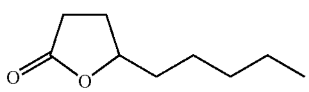 | 5-Pentyl-dihydro-furan-2-one |
| 10 | 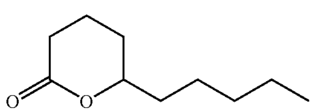 | 6-Pentyl-tetrahydro-pyran-2-one |

TABLE 4

Hydrogenation of esters using $RuCl_2$(L-1)

| Test | Sub. | Conv. (%) | Isolated yield (%) |
|---|---|---|---|
| 1 | 1 | 95 | 81 |
| 2 | 2 | 97 | 91 |
| 3 | 3 | 94 | 82 |
| 4 | 4 | 85 | 61 |
| 5 | 5 | 96 | 83 |
| 6 | 6 | 97 | 89 |
| 7 | 7 | 97 | 88 |
| 8 | 8 | 99 | 93 |
| 9 | 9 | 94 | 91 |
| 10 | 10 | 94 | 86 |

Sub.: Substrate as described in Table 3.

Conv.: Conversion (in %, analysed by GC after silylation) of ester to alcohol after 2 h 30 min.

Reaction conditions: Substrate (20 mmol), $H_2$ gas (50 bars), $RuCl_2$(L-1) 0.05 mol %, NaOMe 10 mol %, THF (14 mL) at 100° C. during 2 h 30 min.

Example 3

Chemoselective Hydrogenation of Esters Using With Complexes of Formula (1)

Hydrogenation of methyl 3-cyclohexene-1-carboxylate was taken as model substrate using complexes $RuCl_2$(L-1) and $RuCl_2$(L-2). Structures of ligands are described in Table 1 and the results are summarised in Table 5.

Typical reaction condition is described below for $RuCl_2$(L-1):

Under argon, a solution of methyl 3-cyclohexene-1-carboxylate (2.810 g, 20 mmol) in THF (2 mL) was added with a syringe, followed by more THF (2×1 mL), to a Keim autoclave equipped with a glass liner containing $RuCl_2$(L-1) (8.4 mg, 0.01 mmol, 0.05 mol %), solid NaOMe (109.7 mg, 2.0 mmol, 10 mol %), and THF (10 mL). Then, the autoclave was pressurised with hydrogen gas at 50 bars and placed in a thermosttated oil bath set at 100° C. After 2 h 30 min, the autoclave was removed from the oil bath, and cooled in a cold-water bath. The glass liner was removed from the autoclave, and the reaction mixture was diluted with citric acid 10% w/w (25 mL) and extracted with MTBE (100 mL). Gas chromatography after silylation showed the following products: methyl 3-cyclohexene-1-carboxylate (2%), cyclohexanemethanol (2%), 3-cyclohexene-1-methanol (91%), 3-cyclohexen-1-carboxylic acid (2%), 3-cyclohexene-1-methyl 3-cyclohexene-1-carboxylate (3%). Purification by flash chromatography on silica gel with pentane/Et$_2$O (10/1→1/1) as elution mixture gave the desired 3-cyclohexene-1-methanol (1.768 g, 15.4 mmol, 77%) as a colorless liquid.

$^1$H NMR (CDCl$_3$, 400 MHz): δ 5.68 (s, AB syst., 2H), 3.57-3.49 (m, AB syst, 2H), 2.2-2 (m, 3H), 1.9-1.7 (m, 4H), 1.35-1.2 (m, 1H).

$^{13}$C NMR (CDCL$_3$, 100 MHz): δ 127.1 (CH), 125.9 (CH), 67.8 (CH2), 36.32 (CH), 28.1 (CH2), 25.2 (CH2), 24.6 (CH2).

TABLE 5

Chemoselectivity observed with complexes of formula (1)

| Test | RuCl$_2$(L-n) | Conv. (%) | Selectivity ROH unsat./ROH sat. | Isolated yield (%) |
|---|---|---|---|---|
| 1 | L-1 | 91 | 98/2 | 77 |
| 2 | L-1 | 84$^{1)}$ | 98/2 | 67 |
| 3 | L-2 | 82 | 97/3 | 66 |

Conv.: Conversion (in %, analysed by GC after silylation) of ester to alcohol after 2 h 30 min.
Reaction conditions: Substrate (20 mmol), H$_2$ gas (50 bars), RuCl$_2$(L-n) 0.05 mol %, NaOMe 10 mol %, THF (14 mL) at 100° C. during 2 h 30 min.
$^{1)}$Reaction run at 80° C. during 5 h.

What is claimed is:

1. A process for the reduction by molecular hydrogenation, of a substrate containing one or two ester or lactone functional groups into its corresponding alcohol or diol, the process comprising reducing said substrate with molecular hydrogen in the presence of a base and at least one catalyst or pre-catalyst in the form of a ruthenium complexes of formula 1 or 2

[Ru(L4)Y$_2$]  (1)

[Ru(L4)(X)$_n$(Y)$_{2-n}$](Z)$_n$  (2)

wherein:
L4 is a ligand of formula (4-A):

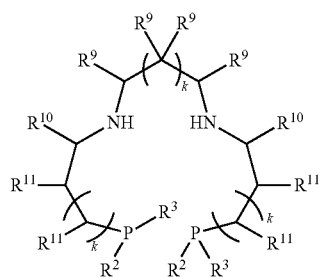

(4-A)

R$^2$ and R$^3$, when taken separately, represent, simultaneously or independently, a linear, branched or cyclic C$_1$ to C$_8$ alkyl or alkenyl group optionally substituted, a C$_6$ to C$_{10}$ aromatic group optionally substituted, or an OR$^{2'}$ or NR$^{2'}$R$^{3'}$ group, R$^{2'}$ and R$^{3'}$ being a C$_1$ to C$_8$ alkyl or alkenyl group; or the groups R$^2$ and R$^3$, when taken together, form a saturated or unsaturated ring optionally substituted, having 4 to 10 atoms and including the phosphorus atom to which the R$^2$ and R$^3$ groups are bonded;
R$^9$, R$^{10}$ and R$^{11}$, taken separately, represent, simultaneously or independently, a hydrogen atom, a C$_1$-C$_8$ linear, branched or cyclic alkyl or alkenyl group optionally substituted or a C$_6$ to C$_{10}$ aromatic group optionally substituted; two adjacent or geminal R$^9$, taken together, may form preferably C$_5$ to C$_8$, ring including the carbon atom to which the R$^9$ groups are bonded; an R$^{10}$ group and an R$^9$ group, in α-position to the same N atom, can be bonded together to form a C$_4$- to C$_6$ ring; two adjacent R$^{11}$ groups can be bonded together to form a C$_6$ to C$_{10}$ aromatic ring optionally substituted or a C$_5$ to C$_{12}$ metallocediyl group optionally substituted and including the carbon atom to which the R$^{11}$ groups are bonded; and k are, simultaneously or independently, equal to 0 or 1;

each Y represents, simultaneously or independently, CO, a hydrogen or halogen atom, a hydroxyl group, or a C$_1$-C$_6$ alkoxy or carboxylic radical, or a BH$_4$ or ALH$_4$ group;

X represents a C$_3$-C$_{30}$ mono-phosphine or a solvent;

Z represents a non-coordinated anion; and n is 0, 1 or 2 and the substrate is a compound of formula (I)

(I)

wherein R$^a$ and R$^b$ represent, simultaneously or independently, a linear, branched or cyclic C$_1$-C$_{30}$ aromatic, alkyl or alkenyl group optionally substituted; or R$^a$ and R$^b$ are bonded together and form a C$_4$-C$_{20}$ saturated or unsaturated group, optionally substituted; and wherein the substituents of R$^a$ and R$^b$ are a COOR$^c$, group, one, two or three halogen, OR$^c$, NR$^c_2$ or R$^c$ groups, in which R$^c$ is a hydrogen atom, a halogenated C$_1$- to C$_2$ groups or a C$_1$ to C$_{10}$ cyclic, linear or branched alkyl, or alkenyl group.

2. The process according to claim 1, wherein the ruthenium complex is of formula

[Ru(L4)Y$_2$]  (1)

wherein L4 and Y have the meaning indicated in claim 1.

3. The process according to claim 1, wherein L4 is a ligand of the formulae (4-D), (4-E), (4-F) or (4-G)

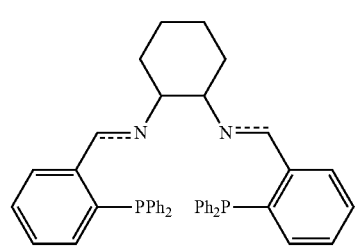

(4-D)

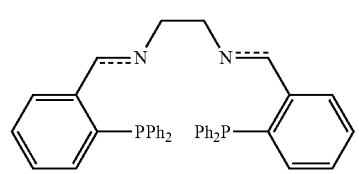

(4-E)

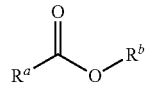
(4-F)

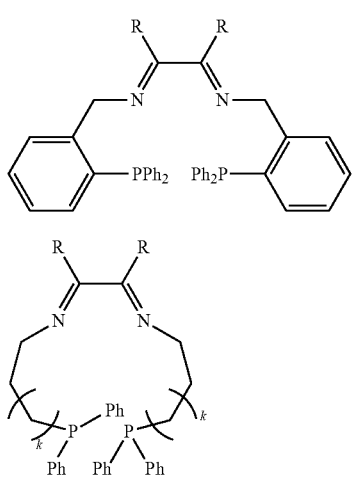
(4-G)

wherein the dotted lines represent a single bond and Ph is phenyl radical, R, taken separately, is $C_1$-$C_5$ alkyl or, taken together, are a $C_3$-$C_6$ group, and each k is, simultaneously or independently, 1 or 0.

4. The process according to claim 1, wherein the base has a $pK_a$ above 14.

5. The process according to claim 1, wherein the base is an alkaline or alkaline-earth metal carbonates, an alkaline or alkaline-earth metal hydroxides, $C_1$- to $C_{10}$ amidures, $C_{10-26}$ phosphazene or an alcoholate of formula $(R^{13}O)_2M$ or $R^{13}OM'$, wherein M is an alkaline-earth metal, M' is an alkaline metal or an ammonium $NR^{14}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical.

6. The ligand N,N'-bis{[2-(diphenylphosphino) phenyl] methylene}-2,2-dimethyl-1,3-propanediamine.

7. A complex of formula (1) or (2)

[Ru(L4)Y$_2$]  (1)

[Ru(L4)(X)$_n$(Y)$_{2-n}$](Z)$_n$  (2)

wherein each Y represents, simultaneously or independently, CO, a hydrogen or halogen atom, a hydroxyl group, or a $C_1$-$C_6$ alkoxy or carboxylic radical, or a BH$_4$ or ALH$_4$ group;

X represents a $C_3$- to $C_{30}$ mono-phosphine or a solvent;

Z represents a non-coordinated anion; and n is 0, 1 or 2, and

L4 is N,N'-bis{[2-(diphenylphosphino)phenyl]methylene}-2,2-dimethyl-1,3-propanediamine.

8. A process for the reduction by molecular hydrogenation, of a substrate containing one or two ester or lactone functional groups into its corresponding alcohol or diol, the process comprising reducing said substrate with molecular hydrogen in the presence of a base and at least one catalyst or pre-catalyst in the form of a ruthenium complexes of formula 1 or 2

[Ru(L4)Y$_2$]  (1)

[Ru(L4)(X)$_n$(Y)$_{2-n}$](Z)$_n$  (2)

wherein L4 is a ligand as defined in claim 6, and each Y represents, simultaneously or independently, CO, a hydrogen or halogen atom, a hydroxyl group, or a $C_1$-$C_6$ alkoxy or carboxylic radical, or a BH$_4$ or ALH$_4$ group;

X represents a $C_3$-$C_{30}$ mono-phosphine or a solvent;

Z represents a non-coordinated anion; and n is 0, 1 or 2 and wherein the substrate is a compound of formula (I)

(I)

wherein $R^a$ and $R^b$ represent, simultaneously or independently, a linear, branched or cyclic $C_1$-$C_{30}$ aromatic, alkyl or alkenyl group optionally substituted; or $R^a$ and $R^b$ are bonded together and form a $C_4$-$C_{20}$ saturated or unsaturated group, optionally substituted; and wherein the substituents of $R^a$ and $R^b$ are a COOR$^c$, group, one, two or three halogen, OR$^c$, NR$^c_2$ or R$^c$ groups, in which R$^c$ is a hydrogen atom, a halogenated $C_1$- to $C_2$ groups or a $C_1$ to $C_{10}$ cyclic, linear or branched alkyl, or alkenyl group.

9. The process according to claim 8, wherein the ruthenium complex is of formula

[Ru(L4)Y$_2$]  (1)

wherein L4 and Y have the meaning indicated in claim 8.

10. The process according to claim 8, wherein the base has a $pK_a$ above 14.

11. The process according to claim 8, wherein the base is an alkaline or alkaline-earth metal carbonates, an alkaline or alkaline-earth metal hydroxides, $C_1$- to $C_{10}$ amidures, $C_{10-26}$ phosphazene or an alcoholate of formula $(R^{13}O)_2M$ or $R^{13}OM'$, wherein M is an alkaline-earth metal, M' is an alkaline metal or an ammonium $NR^{14}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical.

12. A process for the reduction by molecular hydrogenation, of a substrate containing one or two ester or lactone functional groups into its corresponding alcohol or diol, the process comprising reducing said substrate with molecular hydrogen in the presence of a base and at least one catalyst or pre-catalyst in the form of a ruthenium complex of claim 7, and each Y represents, simultaneously or independently, CO, a hydrogen or halogen atom, a hydroxyl group, or a $C_1$-$C_6$ alkoxy or carboxylic radical, or a BH$_4$ or ALH$_4$ group;

X represents a $C_3$-$C_{30}$ mono-phosphine or a solvent;

Z represents a non-coordinated anion; and n is 0, 1 or 2 and wherein the substrate is a compound of formula (I)

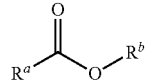
(I)

wherein $R^a$ and $R^b$ represent, simultaneously or independently, a linear, branched or cyclic $C_1$-$C_{30}$ aromatic, alkyl or alkenyl group optionally substituted; or $R^a$ and $R^b$ are bonded together and form a $C_4$-$C_{20}$ saturated or unsaturated group, optionally substituted; and wherein the substituents of $R^a$ and $R^b$ are a COOR$^c$, group, one, two or three halogen, OR$^c$, NR$^c_2$ or R$^c$ groups, in which R$^c$ is a hydrogen atom, a halogenated $C_1$- to $C_2$ groups or a $C_1$ to $C_{10}$ cyclic, linear or branched alkyl, or alkenyl group.

13. The process according to claim 12, wherein the base has a $pK_a$ above 14.

14. The process according to claim 12, wherein the base is an alkaline or alkaline-earth metal carbonates, an alkaline or alkaline-earth metal hydroxides, $C_1$- to $C_{10}$ amidures, $C_{10-26}$ phosphazene or an alcoholate of formula $(R^{13}O)_2M$ or $R^{13}OM'$, wherein M is an alkaline-earth metal, M' is an alkaline metal or an ammonium $NR^{14}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical.

* * * * *

UNITED STATES PATENT AND TRADEMARK OFFICE
CERTIFICATE OF CORRECTION

| | | |
|---|---|---|
| PATENT NO. | : 7,989,665 B2 | Page 1 of 1 |
| APPLICATION NO. | : 11/854906 | |
| DATED | : August 2, 2011 | |
| INVENTOR(S) | : Saudan et al. | |

It is certified that error appears in the above-identified patent and that said Letters Patent is hereby corrected as shown below:

Column 17:
Line 58, change "$OR^{2'''}$" to -- $OR^{2'}$ --.
Line 59, change "$NR^{2'}R3'''$" to -- $NR^{2'}R^{3'}$ --; and change "$R^{2'}$ and $R^{3'''}$" to -- $R^{2'}$ and $R^{3'}$ --.

Signed and Sealed this
Twenty-seventh Day of September, 2011

David J. Kappos
*Director of the United States Patent and Trademark Office*